US011535704B2

(12) United States Patent
Wiese et al.

(10) Patent No.: US 11,535,704 B2
(45) Date of Patent: Dec. 27, 2022

(54) SURGICAL BARRIERS POSSESSING CLINICALLY IMPORTANT ABSORPTION CHARACTERISTICS

(71) Applicant: BVW Holding AG, Cham (CH)

(72) Inventors: Hinrich Wiese, Kaufbeuren (DE);
Joerg Tessmar, Regensburg (DE);
Martina Kessler, Regensburg (DE);
Lukas Bluecher, Eurasburg (DE);
Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 0 days.

(21) Appl. No.: 13/624,101

(22) Filed: Sep. 21, 2012

(65) Prior Publication Data

US 2013/0108821 A1    May 2, 2013

Related U.S. Application Data

(60) Provisional application No. 61/538,159, filed on Sep. 23, 2011.

(51) Int. Cl.

| C08G 63/06 | (2006.01) |
| C08G 18/12 | (2006.01) |
| A61L 31/06 | (2006.01) |
| C08G 18/73 | (2006.01) |
| A61L 31/14 | (2006.01) |

(Continued)

(52) U.S. Cl.
CPC .............. *C08G 63/06* (2013.01); *A61L 31/06* (2013.01); *A61L 31/10* (2013.01); *A61L 31/14* (2013.01); *A61L 31/148* (2013.01); *A61L 31/16* (2013.01); *B32B 3/02* (2013.01); *B32B 3/266* (2013.01); *B32B 27/08* (2013.01); *B32B 38/04* (2013.01); *C08G 18/12* (2013.01); *C08G 18/3203* (2013.01); *C08G 18/3206* (2013.01); *C08G 18/3234* (2013.01); *C08G 18/4018* (2013.01); *C08G 18/428* (2013.01); *C08G 18/4266* (2013.01); *C08G 18/4277* (2013.01); *C08G 18/44* (2013.01); *C08G 18/48* (2013.01); *C08G 18/4833* (2013.01); *C08G 18/4854* (2013.01); *C08G 18/4887* (2013.01); *C08G 18/664* (2013.01); *C08G 18/6674* (2013.01); *C08G 18/73* (2013.01); *C08G 18/755* (2013.01); *C08G 63/66* (2013.01); *C08G 63/664* (2013.01); *C08G 65/2603* (2013.01); *C08L 71/02* (2013.01); *A61L 2300/604* (2013.01); *C08G 2230/00* (2013.01); *C08G 2261/126* (2013.01); *C08L 2205/05* (2013.01); *Y10T 428/239* (2015.01); *Y10T 428/24331* (2015.01); *Y10T 428/31554* (2015.04)

(58) Field of Classification Search
CPC ........ C08G 63/06; C08G 18/73; C08G 63/66;
C08G 18/3203; C08G 18/4018; C08G 18/4854; C08G 65/2603; C08G 18/4266;
C08G 18/755; C08G 18/428; C08G 63/664; C08G 18/4887; C08G 18/4833;
C08G 18/44; C08G 18/3234; C08G 18/4277; C08G 18/48; C08G 18/12;
C08G 2230/00; C08G 2261/126; C08G 18/3206; C08G 18/664; C08G 18/6674;
A61L 31/06; A61L 31/14; A61L 31/148;
A61L 31/16; A61L 31/10; A61L 2300/604; C08L 71/02; C08L 2205/05;
B32B 3/02; B32B 3/266; B32B 27/08;
B32B 38/04; Y10T 428/31554; Y10T 428/239; Y10T 428/24331
See application file for complete search history.

(56) References Cited

U.S. PATENT DOCUMENTS 4,132,839 A    1/1979   Marans et al.
4,988,777 A    1/1991   Hergenrother et al.
(Continued)

FOREIGN PATENT DOCUMENTS

| CA | 2574933 A1 * | 2/2006 |
| WO | WO 98/02171 | 1/1998 |
| WO | WO 99/02168 | 1/1999 |

OTHER PUBLICATIONS

Gorna, K. et al. "In vitro degradation of novel medical biodegradable aliphatic polyurethanes based on epsilon-caprolactone and Pluronics(R) with various hydrophilicities" Polymer Degradation and Stability, vol. 75, No. 1, pp. 113-122 (2001).

(Continued)

*Primary Examiner* — Rabon A Sergent
(74) *Attorney, Agent, or Firm* — Patterson Intellectual Property Law, P.C.; Ryan D. Levy; Mark A. Kilgore

(57) ABSTRACT

The present disclosure provides copolymers useful in medical devices. For example, the disclosure provides copolymers comprising the polymerization product ester block, ether blocks and diisocyanates. In certain embodiments, the disclosure provides a medical copolymer for implantation comprising ester blocks and ether blocks, wherein: the ester blocks comprise a negative free energy transfer and the ether blocks comprise a positive free energy transfer, the ether and ester blocks are less than 1/10 the length of said copolymer, and, the blocks are distributed such that no domain of contiguous blocks possessing the same polarity of free energy transfer are less than 1/3 of the molecular weight of the copolymer. The disclosure further provides methods of making the aforementioned polymers, and medical devices comprising the polymers.

10 Claims, 1 Drawing Sheet

(51) Int. Cl.

| | |
|---|---|
| *C08G 63/66* | (2006.01) |
| *C08G 18/32* | (2006.01) |
| *C08G 18/40* | (2006.01) |
| *C08G 18/48* | (2006.01) |
| *C08G 65/26* | (2006.01) |
| *C08G 18/42* | (2006.01) |
| *C08G 18/75* | (2006.01) |
| *C08G 63/664* | (2006.01) |
| *C08G 18/44* | (2006.01) |
| *A61L 31/16* | (2006.01) |
| *A61L 31/10* | (2006.01) |
| *C08L 71/02* | (2006.01) |
| *C08G 18/66* | (2006.01) |
| *B32B 3/02* | (2006.01) |
| *B32B 3/26* | (2006.01) |
| *B32B 27/08* | (2006.01) |
| *B32B 38/04* | (2006.01) |

(56) References Cited

U.S. PATENT DOCUMENTS

| | | | |
|---|---|---|---|
| 5,019,096 A * | 5/1991 | Fox, Jr. | A61B 42/10 |
| | | | 2/167 |
| 5,208,316 A | 5/1993 | Yoshinaga | |
| 5,266,323 A | 11/1993 | Guthrie et al. | |
| 5,270,044 A | 12/1993 | Fulmer et al. | |
| 5,360,892 A | 11/1994 | Bonsignore et al. | |
| 5,380,813 A | 1/1995 | Seppala et al. | |
| 5,563,238 A | 10/1996 | Bonsignore et al. | |
| 5,665,931 A | 9/1997 | Washiyama | |
| 5,708,073 A | 1/1998 | Dodge et al. | |
| 5,711,958 A | 1/1998 | Cohn et al. | |
| 6,136,333 A | 10/2000 | Cohn et al. | |
| 6,211,249 B1 | 4/2001 | Cohn et al. | |
| 6,258,382 B1 | 7/2001 | Takaoka et al. | |
| 6,346,274 B1 | 2/2002 | Koll et al. | |
| 6,451,346 B1 | 9/2002 | Shah et al. | |
| 6,541,033 B1 | 4/2003 | Shah | |
| 6,555,645 B1 | 4/2003 | Ikeda et al. | |
| 6,579,951 B1 | 6/2003 | Cohn et al. | |
| 6,696,499 B1 | 2/2004 | Cohn et al. | |
| 6,753,384 B2 | 6/2004 | Whitehouse et al. | |
| 6,870,012 B2 | 3/2005 | Cohn et al. | |
| 7,645,823 B2 | 1/2010 | Horie et al. | |
| 7,910,657 B2 | 3/2011 | Cohoon-Brister | |
| 7,964,696 B2 | 6/2011 | Gunatillake et al. | |
| 7,985,414 B2 | 7/2011 | Knaack et al. | |
| 9,480,747 B2 * | 11/2016 | Bluecher | A61K 47/32 |
| 2004/0076673 A1 | 4/2004 | Bateman et al. | |
| 2004/0092695 A1 | 5/2004 | Hu et al. | |
| 2004/0202694 A1 | 10/2004 | Burbank et al. | |
| 2005/0013793 A1 | 1/2005 | Beckman et al. | |
| 2005/0165128 A1 | 7/2005 | Cohn et al. | |
| 2006/0216323 A1 | 9/2006 | Knaack et al. | |
| 2007/0042044 A1 | 2/2007 | Fischer et al. | |
| 2007/0275033 A9 | 11/2007 | Moore et al. | |
| 2007/0292691 A1 | 12/2007 | Chang et al. | |
| 2007/0299227 A1 | 12/2007 | Gopferich et al. | |
| 2009/0060978 A1 | 3/2009 | Bluecher | |
| 2009/0182415 A1 | 7/2009 | Wang | |
| 2010/0034869 A1 | 2/2010 | Tessmar et al. | |
| 2010/0068171 A1 | 3/2010 | Guelcher et al. | |
| 2010/0114328 A1 | 5/2010 | Milbocker et al. | |
| 2010/0129456 A1 | 5/2010 | Ishihara et al. | |
| 2010/0266663 A1 | 10/2010 | Calhoun et al. | |
| 2012/0010726 A1 | 1/2012 | Bluecher et al. | |
| 2012/0039959 A1 | 2/2012 | Tessmar et al. | |

OTHER PUBLICATIONS

Loh, J.L. et al. "Hydrolytic degradation and protein release studies of thermogelling polyurethane copolymers consisting of poly[(R)-3-hydroxybutyrate], poly(ethylene glycol), and poly(propylene glycol)," Biomaterials, vol. 28, pp. 4114-4123 (2007).

Sosnik, A. et al. "Reverse thermo-responsive poly(ethylene oxide) and poly(propylene oxide) multiblock copolymers," Biomaterials, vol. 26, pp. 349-357 (2005).

* cited by examiner

SURGICAL BARRIERS POSSESSING CLINICALLY IMPORTANT ABSORPTION CHARACTERISTICS

CROSS-REFERENCE TO RELATED APPLICATIONS

This application claims the benefit of priority to U.S. provisional application No. 61/538,159, filed on Sep. 23, 2011, the contents of which are hereby incorporated by reference in their entirety.

TECHNICAL FIELD

The present disclosure relates generally to implantable, absorbable medical devices and more specifically to medical devices comprising polymers of ether and/or ester group linked with urethane and/or urea groups for implantation into the living tissue of a mammal, and methods of making the same. More specifically, this disclosure relates to anti-adhesion surgical barriers, which contain many ether and ester groups. And yet more specifically, this disclosure relates to absorbable anti-adhesion surgical barriers, which do not possess certain adverse degradation characteristics, such as macroscopic fracturing of the implant, necrosis due to pH change of the implant, and excessive granulation, encapsulation, or fibrosis.

BACKGROUND

Medical treatments for the shortcomings or functional deficiencies of biological structures have long included sheet structures for the reconstruction, reinforcement and sequestration of tissue defects. These implantable sheet structures are commonly known as anti-adhesion devices. Common failures of implantable anti-adhesion devices include their propensity to disaggregate quickly, fracture into relatively large pieces, cause tissue necrosis as a result of degradation byproducts, and/or induce a chronic inflammatory response. It is the continuous planar form of these devices which enables them to be effective in blocking the formation of tissue adhesions between adjacent tissue surfaces. Therefore a preferred degradation pathway would maintain the planar integrity of the implant while the total mass of the implant is decreasing. Furthermore, it is desirable that the implant disaggregate into pieces of size suitable for phagocytosis in the final phase of absorption.

Macroscopic fracturing, necrosis and inflammation are associated with acute and chronic adverse clinical outcomes. Rapidly absorbing implants comprised of, for example polylactic acid, release hydronium ions, which can acutely cause cellular death and focal tissue necrosis. Chronically, macroscopic fracturing of the implant, together with a local foreign body response, causes loss of barrier functionality and inflammation. Inflammation leads to fibrosis, which can re-initiate chemotactic and cellular processes responsible for adhesion formation that normally subsists after approximately a week post-implantation. Fibrosis, focal to macroscopic pieces of an absorbable implant, leads to encapsulation and the formation of hard, avascular centers, which interfere with normal tissue healing. Excessive fibrosis, and generally the formation of avascular tissue at a repair site, results in a repair that is vulnerable to failure due to the paucity of blood supply, restricted metabolic tissue maintenance and repair processes.

Anti-adhesion implants are typically formed by solution casting or melt extrusion. In both cases the polymeric composition of the implant enters a liquid or mobile phase. In the liquid phase, hydrophobic/hydrophilic regions on polymer chains aggregate with hydrophobic/hydrophilic regions on other polymer chains, respectively. This aggregation can become macroscopic and form micelles. Since hydrophilic regions generally degrade faster than hydrophobic regions, the physiologic absorption process results in macroscopic pieces which are hydrophobic. As a consequence, implants which are globally biocompatible may result in pieces which are far less biocompatible and fibrogenic.

Accordingly, there is a need for anti-adhesion polymeric compositions that do not form macroscopic regions within an implant of significantly varying levels of hydrophobicity. One solution to this problem is to form crosslinks between hydrophobic and hydrophilic regions. Crosslinks in an implant generally reduce the rate of absorption, and may not be suitable for anti-adhesion devices. Furthermore, dissolution of an implant is much preferred to fracturing of an implant regardless of whether the absorption process results in pieces of elevated hydrophobicity. In most cases, employing a crosslinked structure prevents the use of solution casting or extrusion in the manufacture of a device. In this case, the sheet structure of the implant must be made by polymerization casting, which generally is operationally far more difficult and variable in its results.

An alternative to crosslinking the polymeric structure is to select components that are approximately equally hydrophilic. Hydrophobic structures are generally stiff, brittle, and induce a large foreign body response. Hydrophilic structures are generally unstable in living tissue, have low tensile strength, change volume in situ, and/or degrade or dissolve quickly. As a consequence, employing a composite hydrophobic/hydrophilic or amphiphilic structure, or alternatively crosslinking is needed in order to obtain implants with the mechanical and biocompatible characteristics required clinically.

BRIEF SUMMARY

It is one object of the present disclosure to provide a medical assembly suitable for substantially long-term implantation in a host animal, said medical assembly comprising: a surgical barrier aspect at least a portion of which is formed of biodegradable polylactic acid; and a hydrophilic aspect, at least a portion of which is formed of polyethylene glycol; wherein the biodegradable aspect is distributed throughout the polymer with sufficient uniformity to prevent macroscopic fractionation of the implant.

It is another object of the disclosure to provide a medical assembly possessing an ether group which comprises a polymer of said disclosure in sufficient quantity to reduce the flux of lactic acid released into the body by biodegradation as a function of time. This achieved, in an embodiment, by exchanging polyethylene glycol/polylactic acid copolymers with polyethylene glycols attached to polylactic acid (PLA) through urethane links.

It is another object of the disclosure to provide a medical assembly possessing a hydrophilic aspect, which comprises the polymer of said disclosure in sufficient quantity to reduce the fibrotic potential, and accordingly, the foreign body response.

It is another object of the present disclosure to provide a medical assembly suitable for long-term implantation in a host animal, said medical assembly comprising: a surgical barrier aspect, at least a portion of which is formed of biodegradable polylactic acid; a hydrophilic aspect, at least a portion of which is formed of polyethylene glycol; and a linking aspect, comprised of one or more of urea urethane groups, wherein the biodegradable aspect is uniformly distributed throughout the polymer to prevent macroscopic fractionation of the implant.

It is another object of the disclosure to provide a medical assembly suitable for implantation, said assembly comprising prepolymers formed by reacting copolymers of PLA and polyethylene glycol with a diisocyanate, and polymerizing these prepolymers with a chain extender comprising a difunctional or trifunctional polyol and a substance endcapping substance containing one hydroxyl group. Said chain extender portion comprises a ratio of di- and trifunctional polyols and endcapping substance suitable in quantity to obtain, after polymerization, a polymer of a desired mean molecular weight with no pendant isocyanate groups.

It is another object of the disclosure to provide a medical assembly suitable for implantation comprising prepolymers formed by reacting copolymers of, or molecules of, PLA and polyethylene glycol, with a diisocyanate to obtain PLA-urethane-PEG blocks, and polymerizing these prepolymers with a chain extender, said chain extender comprising a difunctional or trifunctional polyol and an endcapping substance containing one hydroxyl group. Alternatively, the chain extender contains PLA.

It is another object of the disclosure to provide a medical assembly comprising a first anti-adhesive layer, a second cell conductive layer and a third structural layer.

It is another object of the disclosure to provide a medical assembly comprising a first anti-adhesive layer, a second cell conductive layer and a third structural layer, wherein said second layer absorbs at a fast rate, said first layer absorbs at a slower rate, and said third layer absorbs at the slowest rate.

It is another object of the disclosure to provide a medical assembly comprising a first anti-adhesive layer, wherein said first anti-adhesive layer is absorbed between 3 weeks and 3 months.

It is another object of the disclosure to provide a medical assembly comprising a second cell culture layer, wherein said second cell culture layer is absorbed between 1 week and 1 month.

It is another object of the disclosure to provide a medical assembly comprising a third structural layer, wherein said third layer is absorbed between 1 month and 1 year.

It is another object of the disclosure to provide methods of fabricating surgical barriers by solution casting or melt annealing.

It is another object of the disclosure to provide surgical barriers that promote cellular ingrowth on one side of the barrier.

In certain embodiments, the present disclosure provides a medical copolymer for implantation comprising ester blocks and ether blocks, wherein: the ester blocks comprise a negative free energy transfer and the ether blocks comprise a positive free energy transfer, the ether and ester blocks are less than $\frac{1}{10}$ the length of said copolymer, and, the blocks are distributed such that no domain of contiguous blocks possessing the same polarity of free energy transfer are less than $\frac{1}{3}$ of the molecular weight of the copolymer.

In other embodiments, the present disclosure provides a medical copolymer of the form $\{\{D_r[A_n(FB_pC_qB_pF)A_n]D_r\}E\}_m$, wherein A is a polymer comprising aliphatic ester units, B is a polyethylene oxide group, C is a polypropylene oxide group, D is derived from a diisocyanate and F is an optional isocyanate, E is a chain extender or crosslinking agent, r is the number of polyester groups, q is the number of contiguous propylene oxide groups, p is the number of contiguous polyethylene oxide groups, n is an integer ranging from 20 to 50, and m is the number of repeating units in the polymer molecule and an integer equal to or greater than 2, preferably ranging from about 2 to about 50, more preferably about 5 to 20. In still other embodiments, the present disclosure provides a medical copolymer of the form $\{\{D_r[A_n(FB_pDC_qDF)]D_r\}E\}_m$ repeating units. In still further embodiments, a medical copolymer comprises the form $\{\{D_r[A_n(FB_pF)A_n]D_r\}E\}_m$ repeating units.

In other aspects of the disclosure a medical assembly comprised of a first anti-adhesion layer, a second cell conductive layer, and a third structural layer, wherein the layers comprise ester and ether blocks that are copolymerized via urethane or urea links.

These and embodiments of the present disclosure are detailed in what follows. It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Figure 1:
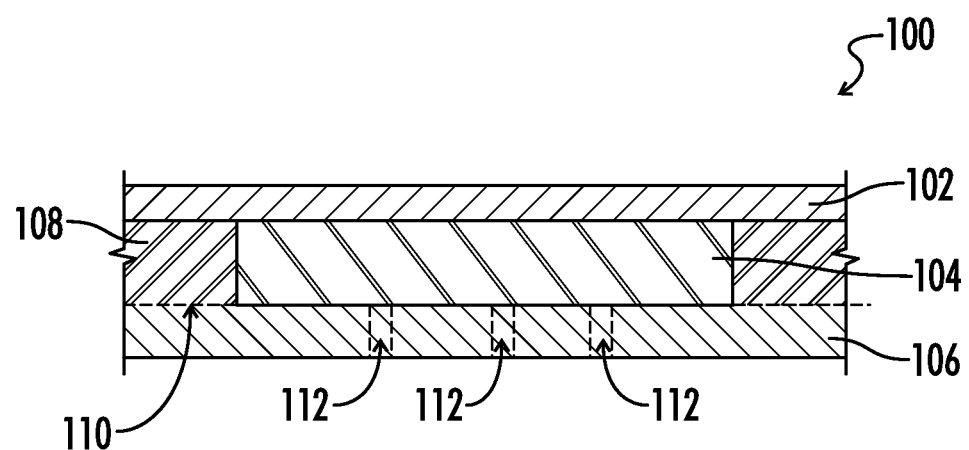
FIG. 1 depicts a surgical barrier of the present disclosure comprising an anti-adhesion surface, a rapidly degrading cellular conductive middle layer, and a structural backing surface.

Reference now will be made in detail to the embodiments of the present disclosure, one or more examples of which are set forth herein below. Each embodiment and example is provided by way of explanation of the polymers, compositions or devices of the present disclosure and is not a limitation. Rather, the following description provides a convenient illustration for implementing exemplary embodiments of the disclosure. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment. Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

Anti-adhesion devices can be used in a number of surgical applications, including: surgical repair of fracture orbital floors, surgical repair of the nasal septum and perforated ear drum micro-membrane, as a protective sheathing to facilitate osteogenesis, surgical repair of the urethral anatomy and repair of urethral strictures, prevention of synostosis in completed corrective surgery for cranial fusions and forearm fractures, lessening of soft-tissue fibrosis or bony growth, as a temporary covering for prenatal rupture omphalocele during staged repair procedures, guided tissue regeneration between the teeth and gingival margin, tympanic membrane repairs, dural coverings and neural repair, heart vessel repair, hernia repair, tendon anastomoses, temporary joint spacers, wound dressings, scar coverings, and as a covering for gastroschisis.

The anti-adhesion device and associated methods of the present disclosure can be, in certain embodiments, particularly suitable for preventing tissue from abnormally fibrotically joining together following surgery, which can lead to abnormal scarring and/or interfere with normal physiological functioning. In some cases, such scarring can force and/or interfere with follow-up, corrective, or other surgical operations.

Accordingly, the present disclosure relates generally to implantable medical devices, and more specifically to medical devices comprising an ether material and a polylactic acid (PLA) material for implantation into living tissue of a host and methods of making the same. More specifically, this disclosure relates to anti-adhesion surgical barriers which degrade biocompatibly. The biocompatible aspect is achieved by minimizing the pH change when the implant degrades in situ, and by reducing the size of the degradation byproducts and macroscopic fracturing of the implant.

A drop in local pH levels due to implant degradation is associated with inflammation, discomfort and foreign antibody responses. Cracked, broken, roughened or flaked surface of an implant can cause tissue turbulence between tissues layers potentially resulting in tissue inflammation and scarring, as well as risking the formation of tissue adhesions, thus defeating the purpose of an anti-adhesion device. Accordingly, in certain embodiments, the present implant materials and devices advantageously are capable of minimizing this pH drop during implant degradation.

This disclosure recognizes the unique advantages of a block copolymer structure with a hydrophobic biodegradable component and a hydrophilic biocompatible component. These structures are bi-functional permitting the selective binding of surface-modifying substances useful in anti-adhesion devices and at the same time suppressive of protein adhesion integral to the formation of tissue adhesions. While not being bound by theory, interactions between cells and implant polymers determine cell growth and cellular infiltration. Natural anchorage mechanisms of the cells are responsible for adhesion of the cells to polymer surfaces. Proteins such as integrins, for example, can be absorbed into a hydrophobic implant surface and allow cells to adhere to the implant surface by binding to specific amino acid sequences. The adhesion of such proteins to biodegradable polymers occurs as a result of proteins from body fluids adsorbing through hydrophobic interactions to the polymer surfaces and, in turn, the cells themselves adhering to the corresponding amino acid sequences of the proteins. This non-specific adsorption of proteins causes a plurality of different cells to adhere to the surface. However, when the hydrophobic and hydrophilic blocks of a polymer are arranged so that hydrophobic interaction with proteins is blocked tissue adhesion mechanisms are mitigated.

In certain embodiments, the present disclosure provides a medical polymer comprising ester blocks and ether blocks. More particularly, in certain embodiments the medical polymer comprises ester blocks and ether blocks copolymerized with diisocyanates, such that the polymer comprises urea and/or urethane linkages. The medical polymers, in certain embodiments, further comprise chain extenders. In certain embodiments, the polymers are the polymerization product of a prepolymer and a chain extender, wherein the prepolymer is formed from the reaction of a diisocyante with an ester/ether copolymer. In some embodiments, the ester block is a PLA, and the ether block is polyethylene glycol, polypropylene glycol, polytetramethylene ether, or a combination thereof.

The prepolymers and optionally the chain extenders of the present disclosure are based on ester diols of α-hydroxy acids or dicarboxylic acids, which optionally contain free radically polymerizable functional group(s) in the backbone. When these chain extenders are used either alone or in combination with conventional chain extenders to form polyurethanes or polyurethane ureas, the polyurethanes degrade at faster rates than those based on conventional chain extenders.

In this disclosure oxides and glycols are not distinguished. Generally, oxides are small molecular weight simple structures called monomers, and must be opened to form polymers or glycols. However, glycols can also be used as building blocks in synthesizing a copolymer. Accordingly, if an oxide is cited as a building block, for example ethylene oxide, then it is to be understood that polymers of ethylene oxide or ethylene glycol are also a suitable building block.

Polyesters, and in particular polylactic acid (PLA), typically degrade in vivo forming byproducts which can adversely alter the local tissue environment. If these implants degrade too quickly, the byproducts cannot be cleared sufficiently quickly and tissue necrosis results.

Polyether polymers, for example polymers containing ethylene glycol and propylene glycol, are not quickly absorbed by the body. In order to make them absorbable, substances such as PLA can be grafted into a polymer backbone comprising ether groups.

In certain embodiments, the urea or urethane groups in the polymers of the present disclosure result in hard segments, and the spacing of the hard segments determines the molecular weight of the degradation byproducts. More preferably, the degradation of hard segments is comparable to the degradation of the soft segments which reduces the occurrence of oligomeric hard segment species among the degradation products. In certain embodiments, ester diols of dicarboxylic acids provide two hydrolysable functional groups within the polymer chain, thereby facilitating rapid break down of the hard segment structure. In further embodiments, polyurethanes or polyurethane ureas based on PEG/PLA structures can be cross linked using a trifunctional chain extender to form network structures with slower degradation rates and greater in vivo stability.

Aromatic polyurethanes and polyurethane ureas possess better mechanical properties than aliphatic polyurethanes. However, their stability makes aromatic polyurethanes less desirable for biomedical applications, especially for applications where degradation of the polymer is required. Polyurethanes release diamines, which originate from the diisocyanate component in the polymer. For example, the diamines that are released upon degradation for commonly used diphenylmethane diisocyanate and toluene diisocyanate based polyurethanes are diaminodiphenylmethane and toluene diamine, respectively. However, possessing some degree of stability in an absorbable polymer can be desirable in certain applications. This secondary stability aspect can be determined by the choice of urea vs. urethane formation within the polymerization. Polyurethane ureas possess better mechanical properties than polyurethanes, due to their higher melting temperature.

Many different diisocyanates are conventionally used in the synthesis of polyurethanes and polyurethane ureas. Both aromatic and aliphatic diisocyanates have been used. In medical applications aliphatic or cycloaliphatic diisocyanates are preferred. Aliphatic diisocyanates for use in the method of the disclosure include, for example, the known aliphatic and cycloaliphatic diisocyanates such as, for example dicyclohexanemethane diisocyanate, 1,4-transcyclohexane-diisocyanate, isophorone diisocyanate (IPDI), hexane diisocyanate and butane diisocyanate.

Polyurethanes and polyurethane ureas obtain their strength and flexibility properties by establishing domains of soft segments and hard segments. The soft segments are generally long ether/ester chains and non-polar, whereas the hard segments are short chains and polar. When polymerized, the hard segments associate due to their charge, creating binding between adjacent polymer chains.

The manner of synthesizing prepolymers and subsequently the final polymer product affects the structure of the polymer and the distribution of the hard and soft segments. For example, in the synthesis of polyurethane ureas, the existence of hydroxyl groups in the prepolymers is important. For example, consider a PEG/PLA diol which is reacted with 2 equivalents of diisocyanate, and subsequently chain extended with a diamine. In this case some of the diisocyanate does not react with the hydroxyl groups of the diol on purely stochastic grounds. However, when the diol is reacted with an excess of diisocyanate every hydroxyl group of the diol is reacted with an isocyanate. Essentially, the excess diisocyanate ensures the reaction of each diol with two molecules of diisocyanate. The excess of diisocyanate must be removed prior to chain extension with the diamine. Furthermore, when an excess of diisocyanate is not used, there is a high probability of the formation of dimers and trimers of the diol. Consequently, when excess diisocyanate is used a smaller size distribution of hard segments is achieved in the chain extension step, resulting in improved mechanical properties. Thus, in certain embodiments, one of the advantages of the present disclosure is that ester groups degrade before urethane groups, and that the soft segment degrades before or at the same time as the hard segment.

In certain embodiments, the present disclosure provides medical polymers of represented by $\{\{D_r[A_n(FB_pC_qB_pF)A_n]D_r\}E\}_m$, wherein A represents a polymer, preferably comprising aliphatic ester units (polyester), B is a polyethylene oxide group, C is a polypropylene oxide group, D is a diisocyanate and F is an optional diisocyanate, E is a chain extender or crosslinking agent, r is the number of polyester groups, q is the number of contiguous propylene oxide groups, p is the number of contiguous polyethylene oxide groups, n is an integer ranging from 20 to 50, and m is the number of repeating units in the polymer molecule and is an integer equal to or greater than 2 (within practical limits, up to about 100,000 or more), preferably ranging from about 2 to about 50, more preferably about 5 to 20. It is also contemplated the numbers m, n, p, q, and r are random but of this general form. In certain embodiments, p, q, and r are, independently for each occurrence, integers greater than 1, for example ranging from 1 to about 100,000, but more preferably, from 1 to about 1000, 1 to about 500, 1 to about 100, or 1 to about 50. In other embodiments, p, q, and r are independently for each occurrence integers ranging from about 5 to about 10,000, about 5 to about 1,000, about 5 to about 50, about 10 to about 50, about 10 to about 1,000, about 10 to about 10,000, about 50 to about 10,000, or about 50 to about 1000.

Thus, certain embodiments relate to a medical copolymer comprising a polymerization product of esters, ethers, diisocyanates and chain extenders such that the polymer comprises at least one segment represented by $\{\{D_r[A_n(FB_pC_qB_pF)A_n]D_r\}E\}_m$. More particularly, in certain embodiments, the medical copolymer comprises a polymerization product of a prepolymer and a chain extender, wherein the prepolymer is a polymerization product of an ester, and ether and a diisocyante. In exemplary embodiments, the ester is a lactide, such as polylactic acid, the ether is polyethylene glycol, polypropylene glycol, or a combination thereof, and the chain extender is a diol or a triol.

In certain embodiments, the polymer comprises urea/urethane links between ether and ester blocks. For example, it may useful to place ether/urea links between ethylene oxide and propylene oxide blocks, for example, of the form $\{\{D_r[A_n(FB_pDC_qDB_pF)A_n]D_r\}\}E_m$.

In certain embodiments, A-blocks suitable for use in the present disclosure are preferably derived from hydroxy acid units or their cyclic dimers and the like, even more preferably α-hydroxy acid units or their cyclic dimers and the like, such as a related ester or lactone. In more particular embodiments, the A block comprises α-hydroxy acid units derived from an aliphatic α-hydroxy carboxylic acid or a related acid, ester or similar compound such as, for example, lactic acid, lactide, glycolic acid, glycolide, or a related aliphatic hydroxycarboxylic acid or ester (lactone) such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-αethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof.

The use of α-hydroxyacids in the present disclosure is preferred in certain embodiments. For example, the A block of the present disclosure preferably comprises a poly(α-hydroxy-carboxylic acid), for example, poly(glycolic acid) (PGA), poly(L-lactic acid), poly(D,L-lactic acid) and polycaprolactone. While not being bound by theory, the aforementioned polymers will degrade and produce monomeric units which may be metabolized by the patient. In further embodiments, the A block comprises PLA, PGA, or a combination thereof. More particularly, the A block comprises PLA.

The hydroxyacids of the present disclosure may be used in combination with other esters, for example, poly-ε-caprolactam, poly-α-hydroxyester, poly-β-hydroxyester, polyanhydride, polyamide, polyphosphazene, polydioxanon, polymalic acid, polytartaric acid, polyorthoester, polycarbonate, and polysaccharide.

The use of alternating blocks of polypropylene oxide and polyethylene oxide is preferred in certain embodiments because they create an amphiphilic backbone of alternating hydrophilic and hydrophobic regions. Where polyethylene is used exclusively, the resulting non-crosslinked polymers are volumetrically unstable and where polypropylene is used exclusively the resulting polymers are fibrogenic.

In alternative embodiments, the polymers comprise ethers other than polypropylene glycol or polyethylene glycol, such as polytetramethylene ether (e.g., terathane).

When the structure of the polymer comprises hydrophobic and hydrophilic blocks, the polymers of the present disclosure have a surfactant-like character. While not being bound by theory, this causes the polymer, e.g. upon contact with an aqueous medium, to be subject to an orientation wherein the hydrophilic component is present in enriched form on the polymer surface pulling water to the surface and creating a veil which mitigates against protein adhesion. Protein adhesion is a primary trigger in foreign body response.

In certain embodiments, an A block is more hydrophobic than a B block when the free energy transfer at the polymer/body interface for substance A is less than substance B. More particularly, a substance is hydrophobic if the free energy transfer is negative and, while a substance is hydrophilic is the free energy positive if it is hydrophilic. There are many methods of measuring hydrophobicity, and associated established scales. As a point of reference, the Wimley-White whole-residue hydrophobicity scale is suitable for selecting polymer constituents of the present disclosure. The scale that measures the energy transfer of unfolded polypeptide chains from water to the bilayer interface (referred to as the Wimley-White interfacial hydrophobicity scale) is appropriate for selecting polymer constituents of the present disclosure.

Accordingly, in certain embodiments, a medical copolymer for implantation comprising ester blocks and ether blocks, wherein: the ester blocks comprise a negative free energy transfer and the ether blocks comprise a positive free energy transfer, the ether and ester blocks are less than $\frac{1}{10}$ the length of said copolymer, and, the blocks are distributed such that no domain of contiguous blocks possessing the same polarity of free energy transfer are less than $\frac{1}{3}$ of the molecular weight of the copolymer. In particular embodiments, the ether blocks comprise ethylene oxide and propylene oxide monomers, and in more particular embodiments, the ethylene oxide monomers and said propylene oxide monomers are present in a number ratio of approximately 3:1. In other embodiments, the ester blocks comprise any A block as defined herein. In still other embodiments, the ethylene oxide monomers and the propylene oxide monomers are linked with urethane or urea groups by copolymerization with a diisocyanate.

Accordingly, in certain embodiments, the medical copolymer comprising ester blocks and ether blocks, herein the ester blocks have a negative free energy transfer and the ether blocks have a positive free energy transfer. In certain embodiments, the ether bocks comprise ethylene oxide and propylene oxide monomers, for example, in a number ratio of approximately 3:1 ethylene oxide to propylene oxide. The ester blocks, in some embodiments, comprise any of the A blocks described herein above, and in particular embodiments, a lactide, such as PLA. In further embodiments, the ester and ether blocks are linked by urea or urethane groups, e.g., they are copolymerized with a diisocyanate.

When polymers have a high ether/ester ratio (e.g. the ratio of ethylene oxide/lactic acid), the blocks have greater mobility, allowing the polyoxyalkylene blocks to associate via hydrophilic attraction and the polylactic acid blocks to associate via hydrophobic exclusion when implanted in living tissue. Though not being bound by theory, while mobility of the hydrophilic blocks is associated with enhanced biocompatibility, domain formation that results in the bulk polymer causes macroscopic fractionation of the implant. By interspersing propylene oxide between the ethylene oxide blocks, mobility (obtained by a high Ether/Ester ratio) is retained without causing domain formation within the bulk polymer.

Chain extended polymers are more likely to enhance phase separation of the distinct ether and ester blocks which comprise the polymer. Therefore it becomes more important that the cumulative effects of any imbalance between hydrophilicity and hydrophobicity caused by chain extension are minimized. In certain embodiments, the polymers of the present disclosure are chain extended with urea or urethane links. These urea and/or urethane hard segments substantially diminish the need for crosslinking. Polymers which are cross-linked (with and without chain extension) are also useful in some embodiments, provided that the crosslinking agent does not enhance domain formation within the bulk polymer and allow for some segmental mobility.

Combinations of ester and ether blocks can take many forms. For example and without limitation, PLA/PGA-ether block copolymers may take the form of one or more of: 1. Poly(L-lactide-co-ether), 2. Poly(L-lactide-co-DL-lactide-co-ether), and 3. Poly(L-lactide-co-glycolide-co-ether).

PLA/PGA-ether-PLA/PGA block copolymers may take the forms of: 4. Poly(L-lactide-co-ether-co-L-lactide), 5. Poly(L-lactide-co-ether-co-L-lactide-co-DL-lactide), 6. Poly(L-lactide-co-ether-co-L-lactide-co-glycolide), 7. Poly (L-lactide-co-DL-lactide-co-ether-co-L-lactide-co-DL-lactide), 8. Poly(L-lactide-co-DL-lactide-co-ether-co-L-lactide-co-glycolide), 9. Poly(L-lactide-co-glycolide-co-ether-co-L-lactide-co-glycolide). Other forms from combinations and/or permutations of the above are envisioned by the present disclosure.

The D block is a urea or urethane formed from the reaction of a diisocyanate with a hydroxy or amine group. Both aromatic and aliphatic diisocyanates are useful, however, aliphatic or cycloaliphatic diisocyanates are preferred in certain embodiments. Aliphatic diisocyanates for use in the method of the disclosure include, for example, known aliphatic and cycloaliphatic diisocyanates such as, for example dicyclohexanemethane diisocyanate, 1,4-transcyclohexane-diisocyanate, isophorone diisocyanate (IPDI), hexane diisocyanate and butane diisocyanate. In particular embodiments, the diisocyanate is isophorone diisocyanate.

The E block is a chain extender used to link together prepolymers of isocyanate endcapped chain of ester (A blocks) and ether (B and C blocks) blocks. When urethane links are desired the chain extender can be a diol. For example, ethylene glycol, diethylene glycol, dipropylene glycol, 1,4-butanediol (BDO), 1,6-hexanediol (HDO), 1,8-octanediol, neopentyl glycol, 1,12-dodecanediol, cyclohexanedimethanol, or 1,4-cyclohexanediol. When urea links are desired, the chain extender can be a diamine. For example, aliphatic diamines including ethylene-; propylene-, butane-, and hexamethylenediamines; cycloaliphatic diamines, such as, for example 1,4-isophorone diamine, and 1,4-cyclohexane diamine. In particular embodiments, E comprises butane diol.

In constructing the AF(BCB) portion of the polymers of the present invention, the diisocyanate linker F is optional. Thus, in certain embodiments, the resulting polymer comprises at least one segment represented by $\{\{D_r[A_n(DB_pC_qB_pD)A_n]D_r\}E\}_m$ (e.g. the optional diisocyanate linker is present), while in other embodiments, the polymer comprises at least one segment represented by $\{\{D_r[A_n(B_pC_qB_p)A_n]D_r\}E\}_m$ (e.g., the optional diisocyanate linker is absent). The ester A block is hydrophobic relative to the ether chain BCB. In certain embodiments, the way in which copolymers of ethylene oxide and propylene oxide are constructed results in a copolymer, which is generally symmetric, either BCB or CBC. When adding hydrophobic symmetric ester groups to hydrophilic symmetric ether groups, it is common for the hydrophobic group to react with both ends of the hydrophilic group, and thus none of the functional end groups are available for further synthesis. In the case of a CBC structure the end propylene C blocks are more hydrophobic relative to the ethylene B blocks, consequently chain extension is not so difficult. In the case of the BCB structure, chain extension is more uniformly achieved if the symmetry of the molecule is broken by adding a different functional group to one end of the BCB. This can be accomplished by modifying one of the hydroxyl groups with an isocyanate or amine group, for example, BCBD. This modification allows the chain extension to be controlled as part of the synthesis such that the chemical reaction only proceeds at one molecule end.

For example, it is possible to polymerize an A block of poly(D,L-lactide) with a BCBD polymer chain where D is an amine group to form ABCBD. This reaction product can be reacted with another BCBD chain to form (BCBD)A(BCBD). Thus, polymers of arbitrary length can be synthesized. The PLA segment is added by ring-opening polymerization from dilactide on the hydroxy end of the BCBD chain.

In general, if the PEG content is greater than the combined ester and propylene glycol content, then the resulting polymer is volumetrically unstable and swells in vivo. In cases where the resulting polymer is less than approximately 20 blocks, the polymer can be water soluble. Water solubility prior to hydrolytic or enzymatic degradation of the copolymer is undesirable in the present disclosure. This behavior can be understood as modifying the hydrophobicity of the polymer.

In certain embodiments, the hydrophobicity of the polymer can be modified by altering the content of the propylene glycol and the generally hydrophobic polyester. The propylene glycol blocks are not biodegradable, whereas the polyester is degradable. Therefore, it is useful to be able to modify the hydrophobicity of the polymer without affecting its biodegradability by modifying the propylene oxide/glycol content.

In further embodiments, the disclosure provides a medical copolymer comprising $\{\{D_r[A_n(FB_pDC_qDB_pF)]D_r\}E\}$, wherein A is a polymer comprising aliphatic ester units, B is a polyethylene oxide group, C is a polypropylene oxide group, D is a diisocyanate and F is an optional diisocyanate, E is a chain extender or crosslinking agent, r is the number of polyester groups, q is the number of contiguous propylene oxide groups, p is the number of contiguous polyethylene oxide groups, n is an integer ranging from 20 to 50, and m is the number of repeating units in the polymer molecule and an integer equal to or greater than 2. Thus, when the optional diisocyanate F is present, the polymer comprises $\{\{D_r[A_n(DB_pDC_qDB_pF)]D_r\}E\}_m$, and when the optional diisocyante is absent, the polymer comprises $\{\{D_r[A_n(B_pDC_qDB_{pD})]D_r\}E\}_m$.

The medical copolymer, in other embodiments, comprises $\{\{D_r[A_n(B_p)A_n]D_r\}E\}_m$ repeating units, wherein A is a polymer comprising aliphatic ester units, B is a polyethylene oxide group, D is a diisocyanate, E is a chain extender or crosslinking agent, r is the number of polyester groups, p is the number of contiguous polyethylene oxide groups, n is an integer ranging from 20 to 50, and m is the number of repeating units in the polymer molecule and an integer equal to or greater than 2, preferably ranging from about 2 to about 50, more preferably about 5 to 20.

In further embodiments, the medical copolymer comprises $\{\{D_r[A_n(FB_pF)A_n]D_r\}E\}_m$ repeating units, wherein A is a polymer comprising aliphatic ester units, B is a polyethylene oxide group, D is a diisocyanate and F is an optional isocyanate, E is a chain extender or crosslinking agent, r is the number of polyester groups, p is the number of contiguous polyethylene oxide groups, n is an integer ranging from 20 to 50, and m is the number of repeating units in the polymer molecule and an integer equal to or greater than 2, preferably ranging from about 2 to about 50, more preferably about 5 to 20.

The A, B C, D and E blocks in each of these embodiments are as described above.

The synthesis methods of the present disclosure include polymerization of diol, diamine, diisocyanate and dicarboxylic acid compounds. Diols are —OH terminated molecules, such as ethylene glycol, butanediol, —OH terminated polycaprolactone chains, polypropylene, —OH terminated polyesters or oligoesters such as —OH terminated polyethylene succinate or polyhexamethyleneadipate, polyfunctional diols such as tartaric acid. The amines are diamines and their isocyanate analogs, for example ethylene diamine, hexamethylene diamine, amino acids, such as lysine. Examples of difunctional carboxylic acid-containing compounds include, for example, succinic acid, sebacic acid, adipic acid, malic acid, orfumaric acid, —COOH terminated polycaprolactone, —COOH terminated polyesters or oligoesters such as —COOH terminated polyethylene succinate or polyhexamethylene adipate.

In some embodiments, these polymers can be terminated with an unreactive or blocking group at one end of the compound, or, alternatively, the compound may simply be end-capped with an unreactive group such as an alkyl, cycloalkyl, aryl, aralkyl or related group.

In some embodiments, the lactide is be copolymerized with PEG or poloxamer by a ring-opening polymerization or, after a copolymer is manufactured by a direct dehydrating polycondensation of lactic acid with the ether and a catalyst for esterification are added thereto to be able to conduct the reaction. In that case, phosphoric acid, benzenesulfonic acid, acid-type ion-exchange resin, etc. may be used as a catalyst for the esterification.

In the case of a ring-opening polymerization, although the materials may be polymerized in a melted state, it is also possible to conduct the polymerization in a solvent which is capable of solubilizing the monomer or the polymer. The lactic acid used therefor may be any of D-, L- and DL-substances or a mixture thereof.

In some embodiments, polymers suitable in the present disclosure possess a ratio of lactic acid and/or glycolic acid (A block), polyethylene glycol (B block) and polypropylene glycol (C block) in a molar ratio of B/C greater than 1, more preferably 3. When the molar ratio of ether glycol (BCB) to lactic acid and/or glycolic acid (A) is less than 15%, the degradation rate of the resulting copolymer is significantly low, even if the BCB block is substantially all ethylene glycol. On the other hand, when the ester molar ratio (molecular weight ratio of ester to ether groups) is more than 70%, the resulting copolymer exhibits a strongly water-soluble property and is not suitable for medical implants of the present disclosure.

Polymers synthesized by copolymerization may require purification, especially regarding unreacted monomers. Dissolving the reaction product in solvent is a common purifying treatment. Suitable solvents include acetone, chloroform, ether, petroleum ether, etc. where the reaction product is dissolved in the solvent and precipitated in water.

Polymers of the present disclosure may, in certain embodiments, be bioactively modified by the addition of therapeutic substances. These substances can be diffused with the bulk polymer, lightly adhered using charge interaction to the polymer surface, or covalently bonding these substances to polymer ends residing within or on the surface of the device. Therapeutic additives that are useful in the devices of the present disclosure include antimicrobial agents such as iodine, sulfonamides, bisbiguanides, cetylpyridium chloride, domiphen bromide [N,N-dimethyl-N-(2-phenoxyethyl)dodecan-1-aminium bromide] or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, cimetidine, eugenol, or hydrocortisone; anesthetic agents such as lidocaine or benzocaine; anti-fungals; and aldehyde derivatives such as benzaldehyde; insulin; steroids; and anti-neoplastics. It is recognized that in certain medical applications, combinations of these agents in the same device may be useful in order to obtain an optimal effect. Thus, for example, an antimicrobial and an anti-inflammatory agent may be combined in a single device to provide combined effectiveness.

The one or more antimicrobial agents may be provided in such an amount of the composition that provides effective antimicrobial properties to the composition. In certain embodiments, the one or more antimicrobial agents may be present in an amount about 0.0001% to about 2.0% by weight of the composition, preferably 0.001% to about 1.0% by weight, and more preferably from about 0.01% to about 0.5% by weight of the composition.

Geometry of Anti-Adhesion Devices: The present disclosure further provides medical devices comprising the polymers described herein. For example, in certain embodiments, polymers of the present disclosure are cast as sheets to be used as absorbable surgical barriers for preventing adhesions post-operatively. These sheets can be positioned on the surgical site by use of tacks, staples, suture and other conventional fixation means. Presently there is emphasis on absorbable fixation devices.

In some cases a surgical barrier can be used both to strengthen a tissue repair and to block tissue adhesions. In this case, part of the surgical barrier may have an extended life in the patient beyond the interval generally considered effective in blocking tissue adhesion formation. This period may exceed the period for which absorbable fixation devices retain structural integrity. Without fixation, the surgical barrier will provide little structure support to the repair site. However, choosing fixation devices with a longer period of persistence in the body may also not be favored since repair site undergo remodeling which can place tension on the surgical barrier at the fixation points.

Accordingly, in some embodiments, the surgical barrier possesses an ingrowth functionality, allowing the device to be incorporated into the wound site for the duration of its life. In order to retain the anti-adhesion effectiveness of the device, the ingrowth functionality should be presented only on the side of the device facing the repaired tissue. Therefore, in those applications of the present disclosure where the implant serves the dual functions of preventing tissue adhesions and providing structure support to the repair site, the device preferably possesses a slippery, generally more rapidly absorbed or modified side and a second slower absorbed side with ingrowth functionality.

For example, in certain embodiments, a medical assembly comprising three layers is provided. One or more of the layers comprise, in certain embodiments, the medical polymers described herein. More particularly, provided herein is a medical assembly comprising an anti-adhesion layer, a cell conductive layer, and a structural layer, wherein the layers comprise polymers of ester and ether blocks that are copolymerized with diisocyanates to form urethane or urea links.

In particular embodiments, the anti-adhesive layer comprises a copolymer comprising the structure $\{\{D_r[A_n(B_p)A_n]D_r\}E\}_m$, the cell conductive layer comprises a copolymer comprising the structure $\{\{D_r[A_n(FB_pC_qB_pF)A_n]D_r\}E\}_m$, wherein the copolymer is terminated with a mono-hydroxyl group, and the structural layer comprises a copolymer comprising the structure $\{\{D_r[A_n(FB_pC_qB_pF)A_n]D_r\}E\}_m$.

In other particular embodiments, the anti-adhesive layer comprises a copolymer comprising the structure $\{\{D_r[A_n(B_p)A_n]D_r\}E\}_m$, the cell conductive layer comprises a copolymer comprising the structure $\{\{D_r[A_n(FB_pC_qB_pF)A_n]D_r\}E\}_m$, wherein the copolymer is terminated with a mono-hydroxyl group, and the structural layer comprises a copolymer comprising the structure $\{\{D_r[A_n(FB_pDC_qDB_pF)]D_r\}E\}_m$.

In other embodiments, the structural layer is perforated. More particularly, in certain embodiments, the anti-adhesion and structural layers are connected along a periphery and separated by a space, this space forming an internal volume, this volume filled with the copolymer of the cell conductive layer, the structural layer comprises perforations, and wherein cellular infiltrates pass through the perforations and invade the internal volume.

Referring now to FIG. 1, a surgical barrier of the present disclosure 100 is illustrated, and comprises an anti-adhesion surface 102, a rapidly degrading cellular conductive middle layer 104, and a structural backing surface 106. The anti-adhesion surface 102 has a residence time in a mammalian body of between 1 week and 1 year, more preferably from 3 weeks to 3 months, and most preferably about 1 month. The cell conductive layer 104 has a residence time in a mammalian body of between 1 day and 1 year, more preferably from 1 week to 1 month, and most preferably about 2 weeks. The structural surface 106 has a residence time in a mammalian body of between 1 month and 5 years, more preferably from 3 months to 3 years, and most preferably about 1 year. In certain embodiments, the anti-adhesion surface suitable in the present disclosure has a A(CBC)A structure, for example as described in EXAMPLE 1, or an AD(BCB)DA structure as in EXAMPLE 3. In some embodiments, the cell conductive layer may have a A(B)A structure, for example as in EXAMPLE 2 or a AD(B)DA structure as in EXAMPLES 6 and 9 or any of these structures terminated with a mono-hydroxyl group as in EXAMPLE 16. In some embodiments, the structural surface may have a (TD[BCB]3)DA structure, for example as in EXAMPLE 4 or an AD(B)DA structure as in EXAMPLES 16-21.

The present disclosure also provides methods of fabricating medical assemblies. For example, the medical assemblies described herein may be fabricated by provide cast layers of the polymers. For example, a method can comprise solution casting the anti-adhesion first layer, solution casting the cell conducive second layer and solution casting the structural third layer. In particular embodiments, a peripheral spacer is placed on the anti-adhesion first layer prior to casting the cell conductive second layer such that a peripheral region of the first layer is blocked. Thus, the second layer is solution casted within the peripheral spacer, and the spacer is then removed. The third layer is placed the second layer. In particular embodiments, the third layer may be solution casted and perforated prior to placing it on the second layer. More particularly, a method of fabricating a medical assembly comprises the steps of: a) forming a solution casted first layer, b) placing a peripheral spacer on the first layer, such that a peripheral region of the first layer is blocked, c) forming a solution casted second layer over the first layer and within the peripheral spacer, d) removing the peripheral spacer, e) forming a solution casted third layer, f) perforating the third layer, g) pouring a solution of the copolymer comprising the third layer into the peripheral region and removing the solvent, h) applying a solution of copolymer comprising the third layer on the second layer, i) placing the perforated third layer over the second layer and polymer solution, and j) removing solvent in the assembly to bond the third layer to the second layer. An alternative method comprises the steps of: a) forming a solution casted first layer, b) forming a spacer comprising a solution casted third layer that blocks a peripheral region of the first layer, c) forming a solution casted second layer of shape and size to fit within the spacer, d) forming a solution casted third layer, and e) contacting the layers to provide the medical assembly, wherein the assembly comprises the first layer, a second layer comprising the second layer placed within the spacer and the third layer. The contacting of the three layers may comprise bonding the layers using heat, pressure, or both. In a particular embodiment, the third layer is perforated.

Referring again to FIG. 1, the 3-layer structure of 100 can be formed by successive solution casts of the polymers described herein using a volatile solvent, for example, acetone. For example, a first anti-adhesion layer 102 is formed by pouring solubilized polymer into a form, such as a petri dish. The solvent is driven off, and a ring form is placed in the petri dish such that a peripheral region of the anti-adhesion layer is blocked. Then a second cell conductive layer 104 is formed by pouring solubilized polymer into the interior of the ring form and the solvent is driven off. Subsequently, the ring form is removed, creating step structure 108. A third structural layer 106 is formed in two parts. First, a connection 110 is formed by pouring solubilized polymer over this structure, completely filling the step structure 108. Second, in a separate form, the third structural layer 106 is formed by pouring solubilized polymer into the form to make a single layer. The solvent is driven off and the third layer 106 is removed from the second form and this layer 106 is perforated 112. The perforation 112 can be achieved by mechanical punch or by laser. Perforated layer 106 is applied over formed layers 102 and 104 by applying solubilized polymer between layers 104 and 106, thus bonding layer 106 to the construct of layers 102 and 104. Preferably, the solubilized polymer used to bond layer 106 to 104 is the same solubilized polymer used to form layer 106. The solvent is driven off, and a connection 110 is formed between first anti-adhesion layer 102 and third structural layer 106.

Figure 2:
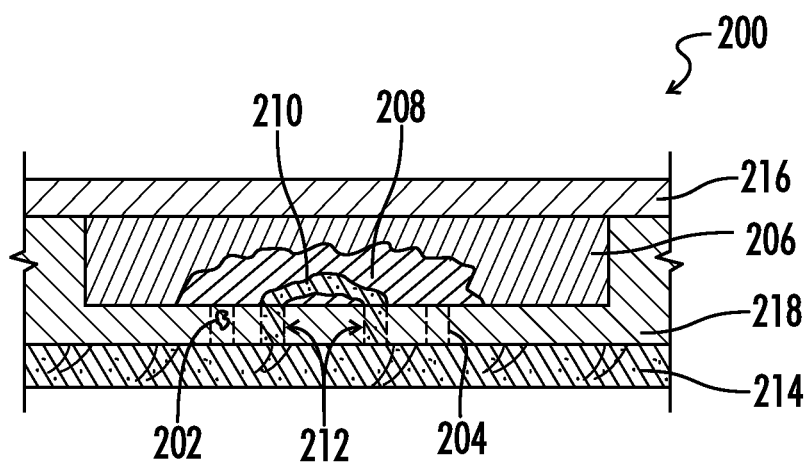
FIG. 2 depicts the tissue ingrowth functionality of a surgical barrier of the present disclosure comprising an anti-adhesion surface, a rapidly degrading cellular conductive middle layer, and a structural backing surface.

Referring now to FIG. 2, the ingrowth functionality 200 of a surgical barrier is illustrated. Cellular infiltrates 202 enter perforations 204. The cells enter fast degrading polymer layer 206 and solubilize polymer layer 206 and initiate fibrin deposition and cellular ingrowth. Cellular ingrowth includes formation of extracellular matrix, structural cells, and neovascularization. The result is a vascularized, living region 208 forming tissue bridges 210 between pores 212 and tissue 214. In time, polymer layer 206 is completely replaced with tissue. This tissue ingrowth fixes surgical barrier 200 to the wound site. At a further time subsequent to tissue ingrowth, anti-adhesion layer 216 is absorbed leaving a layer of mature tissue resistant to tissue adhesion formation. Structural layer 218 remains fully incorporated in the tissue ingrowth, and provides structural reinforcement to the surgical repair site.

In certain embodiments, the surgical barriers can be further enhanced by attaching bioactive substances to the surfaces of the present disclosure. For example, the anti-adhesive surface may comprise attached anti-microbials, and the structural surface may comprise attached angiogenic molecules.

To increase the biocompatibility of the polymer surfaces in certain embodiments, asymmetric molecules can be bonded onto these surfaces, for example via radical mechanisms. For example, these asymmetric molecules are to be bound to surfaces of a surgical barrier of the present disclosure which firstly adsorb on the polymer surface and then are cross-linked to a bioactive substance. These molecules can be, for example, polyalkylimine or polyalkylamine.

In certain embodiments, substances for cellular controlled are included in the medical assembly. The substances for cellular control are typically chemotactic substance for influencing cell-migration, such as an inhibitory substance for influencing cell-migration, a mitogenic growth factor for influencing cell proliferation and/or a growth factor for influencing cell differentiation. Such substances may be disposed on and/or impregnated within the membrane, but may also be coated on one or more surfaces of the surgical barrier. These surfaces include the interior surfaces of the anti-adhesive layer and the structural layer exposed by solubilization of the cell conductive layer.

In addition, substances may be incorporated in the layers, which may be effective to facilitate selective release of the substances when the surgical barrier is implanted in a patient.

In some embodiments, surfaces of the present disclosure carry functional groups to which bioactive substances may be chemically bonded. These functional groups are in certain embodiments readily accessible to achieve clinically significant chemical bonding. Certain embodiments of the biodegradable polymers of the present disclosure contain polyhydroxyesters such as polylactide, poly(lactide-co-glycolide), etc., which have suitable functional groups at both molecule ends. However, these groups are not readily accessed on the polymer surface. Polylactide, for example, has alcohol and carboxylic acid end groups which inhibit bioactive substances from binding to the polymer surface. In one embodiment, a surface-modified block copolymer has an additional component comprising a surface-modifying substance, which is bonded by means of a reactive group functioning as a binding link.

In some instances, the end group should be hydrophilic, which the ester group is typically not. Therefore, one end of the ether chain is not endcapped with an ester. For example, a polymer with a trifunctional structure may have two arms endcapped with lactide and a third arm with a terminating ethylene glycol. The ethylene glycol arm may be particularly long relative to the lactide endcapped arms such that these ethylene glycol arms orient within the polymer in its solubilized state during casting such that the ethylene glycol arms project out of the polymer surface. This orientation of the hydrophilic arms ensures an adequate distance between the polymer surface and reactive group enabling the binding of surface-modifying substances to the reactive group.

Various catalysts may be used in the binding process, for example, stannous 2-ethylhaxanoate, dibutyltin dilaurate, stannous chloride, stannic chloride, diethylzinc, basic zinc carbonate, titanium tetraisopropoxide, tributyltin methoxide, dibutyltin oxide and aluminum isopropoxide.

In some embodiments, bioactive agents suitable for use with surgical barriers of the present disclosure include without limitation angiogenic factors, growth factors, hormones, anticoagulants, for example heparin and chondroitin sulphate, fibrinolytics such as tPA, plasmin, streptokinase, urokinase and elastase, steroidal and non-steroidal anti-inflammatory agents such as hydrocortisone, dexamethasone, prednisolone, methylprednisolone, promethazine, aspirin, ibuprofen, indomethacin, ketoralac, meclofenamate, tolmetin, calcium channel blockers such as diltiazem, nifedipine, verapamil, antioxidants such as ascorbic acid, carotenes and alpha-tocopherol, allopurinol, trimetazidine, antibiotics, including noxythiolin and other antibiotics to prevent infection, prokinetic agents to promote bowel motility, agents to prevent collagen crosslinking such as cis-hydroxyproline and D-penicillamine, and agents which prevent mast cell degranulation such as disodium chromoglycate, among numerous others.

Polypeptides are also useful bioactive substances, for example, nerve growth factors, epidermal growth factors, fibroblast-derived growth factors, platelet-derived growth factors, colony stimulating factors, erythropoietin, interleukin-1, -2 and -3, interferon-$\alpha$, -$\beta$ and $\gamma$, cartilage-derived factor, cartilage-derived growth factors, bone-derived growth factors, bone morphogenetic proteins, pelvic growth factors, transforming growth factors, insulin and prostaglandin. Others include, IGF, EGF, TGF, BMP and basic FGF, proteins and glycoproteins of the extracellular matrix such as fibronectin, collagen, laminin, bone sialo protein and hyaluronic acid.

Several hormones are useful bioactive substances, for example, somatostatin and its derivatives, growth hormones, prolactin, adrenocorticotropic hormone, melanocyte stimulating hormone, thyrotropin releasing hormone and salts and derivatives thereof, thyroid stimulating hormone, luteinizing hormone, follicle stimulating hormone, vasopressin and derivatives thereof, oxytocin, calcitonin, parathyroid hormone, glucagon, gastrin, secretin, cholecystokinin, angiotensin, human placental lactogen, human chorionic gonadotropin, enkephalin and derivatives thereof, endorphin, kyotorphin, tuftsin, thymopoietin II, thymosin, thymostimulin, thymic humoral factor, serum thymic factor and derivatives thereof as well as other thymic factors, tumor necrosis factor, colony stimulating factor, motilin, neurotensin, caerulein, urokinase, asparaginase, kallikrein, substance P, blood coagulation factors VIII and IX, lysozyme chloride, polymyxin B, colistin, gramicidin and bacitracin.

Prevention of fractionation: A key feature of some embodiments of the polymers of the present disclosure, which differs from other ether-ester copolymers, is their mode of dissolution in a mammalian body. The preferred degradation pathway is dissolution of the polymer at the molecular level, avoiding macroscopic disaggregation of the polymer. This desired dissolution pathway is achieved by one or more of the following considerations: a) avoidance of macroscopic hydrophobic regions within the polymer, b) utilization of crosslinking or multifunctional structures, c) creation of hard centers in the polymer chains to create a pseudo-crosslinks, and d) utilization of hydrophilic PEG as terminal groups to attach bioactive substances which enhance enzymatic degradation over hydrolytic degradation.

Control of size and distribution of hydrophobic regions within the polymer can be achieved by utilizing urethane or urea links to step-wise build alternating hydrophilic and hydrophobic regions. This can be done with the ethers, alternating hydrophilic ethylene oxide blocks and hydrophobic propylene oxide blocks joined by urethane links, or polymerized directly. Alternatively, a desired distribution of hydrophobic regions can be achieved by polymerizing ester blocks and ether blocks through the formation of urethane or urea links.

Any of the described polymers of the present disclosure can be triolized by linking difunctional structures to a triol through urethane or urea links. These trifunctional polymers can be further crosslinked to other di- or tri-functional structures through additional urethane or urea links.

Hard centers in a polymer, especially those residing in polymers which are not crosslinked, tend to associate and form charge mediated bonds. Urethane links form hard centers, thus the addition of urethane links can achieve resistance to macroscopic dissolution without crosslinking. This can be an important consideration in manufacture of surgical barriers of the present disclosure, since crosslinked polymers cannot be solution or melt cast.

Finally, the position of hydrophilic groups importantly determines the degradation pathway. As described, these groups can be associated with bioactive substances that can be used to direct cellular interaction with the implant. Alternatively, hydrophilic groups tend to draw water into the polymer matrix, swelling the polymer, and mobilizing the polymeric chains. This can provide a solubility degradation path without chain cision. Care must be taken to prevent elution of the hydrophilic content of the polymer, which can result in the hydrophobic content remaining and subsequent macroscopic fracturing. Increase in the hydrophobicity of the implant through degradation can be avoided by ensuring there are not separate polymeric chains of significantly different polarity.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in surgical barriers.

As used herein, the term "about" should be construed to refer to both of the numbers specified in any range. Any reference to a range should be considered as providing support for any subset within that range.

Examples are provided to illustrate some embodiments of the polymers and medical devices of the present disclosure but should not be interpreted as any limitation thereon. Other embodiments within the scope of the claims herein will be apparent to one skilled in the art from the consideration of the specification or practice of the compositions, devices, or methods disclosed herein. It is intended that the specification, together with the examples, be considered to be exemplary only, with the scope and spirit of the disclosure being indicated by the claims which follow the example.

EXAMPLES

All chemicals listed were obtained from Sigma-Aldrich (Milwaukee, Wis.) unless otherwise indicated. In the examples that follow, the recipes are directed to making the simplest block structure of the examples featured. It should be understood that, as is common in the art, varying the ratio of ingredients can generate chains containing multiple blocks and thus chains of arbitrary length.

Example 1

Synthesis of an A(BCB)A Block of Poloxamer and Polylactic Acid

Pluronic 31R1 (molecular weight 3250) (BASF, Mt. Olive, N.J.), a copolymer of propylene oxide and ethylene oxide, was dried under vacuum at 85° C. for 12 hr. in a spherical flask, the final water content obtained was below 300 ppm. Ten grams of Pluronic 31R1 was added to 2.1 grams (1)-Lactide and 0.18 grams catalyst (stannous 2-ethyl hexanoate) (0.43%). The reaction was carried out in a sealed flask, under a dry nitrogen saturated atmosphere, for two and half hours at 145° C. The product is a copolymer of Pluronic and polylactic acid.

Example 2

Synthesis of A(B)A Block of Polyethylene Glycol and Polylactic Acid

Polyethylene glycol (molecular weight 3000) was dried in vacuo overnight at 85° C. Thereafter, the PEG was cooled down to room temperature, and the product capped with dry nitrogen. 100 grams of PEG was added to 18 grams (1)-Lactide and 0.18 grams catalyst (stannous 2-ethyl hexanoate). The mixture of PEG and lactide is placed in an oil bath under flowing nitrogen at 140° C. and mixed for 3 hours. At the end of the 3 hour period, the mixture was removed from the oil bath, allowed to cool, dissolved in chloroform and precipitated in ether. The precipitate is thereafter collected and dried overnight in vacuo at 50° C.

Example 3

Synthesis of AD(BCB)DA Block of Poloxamer and Polylactic Acid

In a reactor equipped with stir rod, place 2 moles of diisocyanate under nitrogen. Heat the volume to 60° C. and slowly add 1 mole of poloxamer diol (BCB). The poloxamer should be added at a rate slow enough such that the volume temperature does not rise above 65° C. If the poloxamer is a solid at 60° C., then a solvent can be used. When all the poloxamer has been added to the reaction volume the mixture should be reacted until the isocyanate content corresponds to two available NCO groups per poloxamer molecule. Adding the poloxamer slowly ensures that each poloxamer molecule is endcapped with two diisocyanate molecules, because the majority of the reaction is done in an excess of diisocyanate, and chain extension of the poloxamer is less probable. If prevention of chain extension is important a large excess of diisocyanate can be employed, and the excess diisocyanate evaporated at the termination of the reaction.

Once the poloxamer diisocyanate is prepared as described above, 1 mole can be loaded into a reactor under nitrogen and heated to 85° C., and then two moles of dilactide (A) or another ester are added slowly, and as before preventing an excessive exotherm. The result is a AD(BCB)DA block of poloxamer and polylactic acid.

An arbitrary number of such blocks can be joined together by using fewer A-blocks. For example, blocks of AD(BCB)DAD(BCB)DA can be formed by adding 3 moles of A-block to 2 moles of (BCB)-block. In some cases where a very long chain is desired, it may be more practical to form shorter chains, such as AD(BCB)DAD(BCB)DA, and polymerize these together with additional diisocyanate. For example, to form AD(BCB)DAD(BCB)DADAD(BCB)DAD(BCB)DA, one mole of diisocyanate is added to 2 moles of AD(BCB)DAD(BCB)DA.

Example 4

Synthesis of (TD[BCB]$_3$)DA Block of Poloxamer and Polylactic Acid

While poloxamers of many varied combinations of ethylene oxide (B) and propylene oxide (C) are commercially available, there are practical limits on constructing these chains with monomeric ethylene oxide and propylene oxide. Greater control is afforded by starting with diisocyanates of the monomers, for example DBD or DCD. To these B or C can be arbitrarily added in any combination by forming urethane links between the addition monomer and the diisocyanate end capped chain. Through a step-wise sequence of chain extensions with monomers and subsequent end capping with diisocyanate, any combination of B and C can be obtained. One drawback is that the resulting polymer will be more hydrophobic that a chain obtained by direct polymerization of ethylene oxide and propylene oxide. However, this drawback can be compensated in most cases by using less propylene glycol.

Multi-armed polymers can be constructed without cross-linking by introducing a chain extender E, in this example a triol (T), and linking the triol to poloxamer chains with diisocyanate. For example, poloxamer chains are introduced into a reactor and endcapped with diisocyanate. The resulting poloxamer diisocyanate is then reacted with a low molecular weight triol such a trimethylolpropane. The result is a poloxamer triisocyanate which then can be reacted with ester (A). Preferably, the ester is polylactic acid.

Example 5

Absorbable Polyurethane

In a 3-neck flask are placed 4 g of a PLA-Diol (Mn=1000) and 2 g of Terathane 2000 (Invista, Wichita, Kans.). Toluene is added in excess, and the mixture gently heated to remove toluene to obtain a 20% w/w solution. After cooling to room temperature, 4.5 g of isophorone diisocyanate was added and mixed under dry nitrogen. To the mixture was then added 0.67 g of dibutyltin-dilaurate (DBTL) and the mixture was heated to 75° C. After 5 hours, 1.287 g of 1,4-butane diol is added and the reaction mixture is diluted with toluene to get concentration of all components of approximately 15% Subsequently, the temperature is raised to 80°s C. After 10 hours the mixture is allowed to cool to room temperature. The resulting polymer is precipitated in pentane and dried in vacuo.

Example 6

Absorbable Polyurethane

In a 3-neck flask are placed 4 g of a polylactic acid diol ("PLA diol") (Mn=1000) and 4 g of polyethylene glycol (Mn=2000). Toluene is added in excess, and the mixture is gently heated to remove toluene to obtain a 20% w/w solution. After cooling to room temperature, 4.5 g of isophorone diisocyanate was added and mixed under dry nitrogen. To the mixture was then added 0.67 g of dibutyltin-dilaurate (DBTL) and the mixture was heated to 75° C. After 5 hours, 1.285 g of 1,4-butane diol is added and the reaction mixture is diluted with toluene to get a final concentration of all components of approximately 15%. Subsequently, the temperature is raised to 80° C. After 10 hours the mixture is allowed to cool to room temperature. The resulting polymer is precipitated in pentane and dried in vacuo.

Example 7

Absorbable Polyurethane

In a 3-neck flask are placed 4 g of a PLA-Diol (Mn=1000) and 4 g of polyethylene glycol (Mn=2000). Toluene is added in excess, and the mixture gently heated to remove toluene to obtain a 20% w/w solution. After cooling to room temperature, 4.0 g of isophorone diisocyanate was added and mixed under dry nitrogen. To the mixture was then added 0.65 g of dibutyltin-dilaurate (DBTL) and the mixture was heated to 75° C. After 5 hours, 1.083 g of 1,4-butane diol is added and the reaction mixture is diluted with toluene to get a final concentration of all components of approximately 15%. Subsequently, the temperature is raised to 80° C. After 10 hours the mixture is allowed to cool to room temperature. The resulting polymer is precipitated in pentane and dried in vacuo.

Example 8

Absorbable Polyurethane

In a 3-neck flask are placed 4 g of a PLA-Diol (Mn=1000) and 5 g of polyethylene glycol (Mn=2000). Toluene is added in excess, and the mixture is gently heated to remove toluene to obtain a 20% w/w solution. After cooling to room temperature, 4.12 g of isophorone diisocyanate was added and mixed under dry nitrogen. To the mixture was then added 0.67 g of dibutyltin-dilaurate (DBTL) and the mixture was heated to 75 deg. C. After 5 hours, 1.095 g of 1,4-butane diol is added and the reaction mixture is diluted with toluene to get a final concentration of all components of approximately 15%. Subsequently, the temperature is raised to 80 deg. C. After 10 hours the mixture is allowed to cool to room temperature. The resulting polymer is precipitated in pentane and dried in vacuo.

Example 9

Absorbable Polyurethane

In a 3-neck flask are placed 7.65 g of a PLA-Diol (Mn=1000) and 7.65 g of polyethylene glycol (Mn=2000). Toluene is added in excess, and the mixture is gently heated to remove toluene to obtain a 20% w/w solution. After cooling to room temperature, 8.55 g of isophorone diisocyanate was added and mixed under dry nitrogen. To the mixture was then added 1.28 g of dibutyltin-dilaurate (DBTL) and the mixture was heated to 75° C. After 5 hours, 2.45 g of 1,4-butane diol is added and the reaction mixture is diluted with toluene to get a final concentration of all components of approximately 15%. Subsequently, the temperature is raised to 80° C. After 10 hours the mixture is allowed to cool to room temperature. The resulting polymer is precipitated in pentane and dried in vacuo.

Example 10

Absorbable Polyurethane

In a 3-neck flask is placed 21.0 g of Terathane 2000. Toluene is added in excess, and the mixture gently heated to remove toluene to obtain a 20% w/w solution. After cooling to room temperature, 7.14 g of isophorone diisocyanate was added and mixed under dry nitrogen. To the mixture was then added 0.84 g of dibutyltin-dilaurate (DBTL) and the mixture was heated to 75° C. After 5 hours, 1.93 g of 1,4-butane diol is added and the reaction mixture is diluted with toluene to get concentration of all components of approximately 15%. Subsequently, the temperature is raised to 80 deg. C. After 10 hours the mixture is allowed to cool to room temperature. The resulting polymer is precipitated in pentane and dried in vacuo.

Example 11

Absorbable Polyurethane

In a 3-neck flask is placed 4 g of a PLA-Diol (Mn=2000), 2.0 g of Terathane 2000 and 2 g of polyethylene glycol (Mn=2000). Toluene is added in excess, and the mixture gently is heated to remove toluene to obtain a 20% w/w solution. After cooling to room temperature, 4.05 g of isophorone diisocyanate was added and mixed under dry nitrogen. To the mixture was then added 0.67 g of dibutyltin-dilaurate (DBTL) and the mixture was heated to 75° C. After 5 hours, 1.285 g of 1,4-butane diol is added and the reaction mixture is diluted with toluene to get concentration of all components of approximately 15%. Subsequently, the temperature is raised to 80 .deg. C. After 10 hours the mixture is allowed to cool to room temperature. The resulting polymer is precipitated in pentane and dried in vacuo.

Example 12

Absorbable Polyurethane

In a 3-neck flask was placed 2.0 g of a PLA-Diol (Mn=2000), 2.0 g of polycaprolactone (Mn=2000) and 4.0 g of polyethylene glycol (Mn=2000). Toluene is added in excess, and the mixture gently heated to remove toluene to obtain a 20% w/w solution. After cooling to room temperature, 4.05 g of isophorone diisocyanate was added and mixed under dry nitrogen. To the mixture was then added 0.67 g of dibutyltin-dilaurate (DBTL) and the mixture was heated to 75 deg. C. After 5 hours, 1.285 g of 1,4-butane diol is added and the reaction mixture is diluted with toluene to get concentration of all components of approximately 15%. Subsequently, the temperature is raised to 80 deg. C. After 10 hours the mixture is allowed to cool to room temperature. The resulting polymer is precipitated in pentane and dried in vacuo.

Example 13

Mechanical and Absorption Testing

All degradation studies were carried out under conditions similar to those encountered in vivo. The samples were stored in phosphate buffer solution at 37° C. To determine whether crystallization occurred, the samples were regularly (at the beginning of every hour, then twice daily, and later daily) optically assessed. All sample were initially transparent; crystallization was indicated by internal scattering. Weekly determinations were made of the mechanical properties and the molecular weight.

The following samples were chosen for the research because their original mechanical properties appear interesting: all polyurethanes are ether ester with IPDI 3 as a diisocyanate and are with butanediol chains prolonged. Examples 5, 6, 9 and 10 were tested.

Testing of the Polymer of Example 5
molecular weight: (initial) 31000; (after 1 week) 15500
elongation at break: (initial) 700%; (after 1 week) 760%
tensile strength: (initial) 65 MPa; (after 1 week) 42 MPa
Optical: after 1 week samples are slightly cloudy, the form is unchanged Testing of the Polymer of Example 6
molecular weight: (initial) 11000; (after 1 week) 9650
elongation at break: (initial) 960%; (after 1 week) 0%
tensile strength: (initial) 42 MPa; (after 1 week) 0 MPa
Optical: Sample is clear after a week, but is too friable to remove for assessment Testing of the Polymer of Example 9
molecular weight: (initial) 12500; (after 1 week) 10000
elongation at break: (initial) 1330%; (after 1 week) 105%
tensile strength: (initial) 14.7 MPa; (after 1 week) 0.37 MPa
Optical: Sample is clear after a week, but is too friable to remove for assessment Testing of the Polymer of Example 10
molecular weight: (initial) 15000; (after 1 week) 12500
elongation at break: (initial) 1405%; (after 1 week) 164%
tensile strength: (initial) 16.1 MPa; (after 1 week) 0.23 MPa
Optical: The sample is crystal clear, not visibly damaged, but also very soft Testing of the polymer of Compositions comprising polyethylene glycol (PEG) as the ether segment break down very quickly. Their mechanical properties are very weak after a week in buffer solution, although the molecular weight is not always significantly changed. Only EXAMPLE 5 comprising a polytetramethylene glycol as the ether block showed a significant reduction in the molecular weight and the mechanical properties did not change as quickly as those samples comprising PEG blocks.

Example 14

Synthesis of A(B)A Block of Polyethylene Glycol and Polylactic Acid

This polymer is suitable for use in anti-adhesion devices described subsequently in the present disclosure. PEG-PLA copolymers were synthesized according to the previously described ring opening polymerization scheme. For this synthesis a defined amount of linear or branched PEG was dissolved in 250 ml of toluene and heated to the boiling point in order to remove the azeotrope. About 50 ml of toluene and water residue were removed with a dean stark trap to get a water-free polymer solution. Accordingly weighed amounts of L-dilactide and RL-dilactide (70:30), calculated on the amount of PEG and the desired molecular weight of the copolymer, were also dissolved under heating in 250 ml of toluene and again 50 ml of toluene and residual water was removed. The water-free solution of PEG and dilactide was then combined in a three-necked-flask and heated under a mild nitrogen flow and continuous stirring. One hundred milligrams of stannous octoate were subsequently added to initiate the polymerization. The solution was refluxed over night. On the following day the solution was transferred into a round flask and the toluene was removed using a rotary evaporator. The polymer was then redissolved in methylene chloride and removed again with a rotary evaporator to get rid of remaining toluene residues. This procedure was repeated one more time. After that the polymer was dissolved in a small amount of methylene chloride to form a highly viscous polymer solution. This viscous solution was then added dropwise to an ice-cold mixture of diethylether and methanol (60:40) to precipitate the polymer and remove the stannous octoate catalyst. After filtration of the precipitate, the polymer was lyophilized and the obtained yield was determined.

Copolymers were made using the following ingredient amounts.

| Polymer | PEG (10,000 D) (g) | Dilactide (g) |
|---|---|---|
| PLA35PEG10PLA35 | 6.25 | 43.75 (35,000 D) |
| PLA45PEG10PLA45 | 5.00 | 45.00 (45,000 D) |
| PLA65PEG10PLA65 | 3.57 | 46.43 (65,000 D) |

Example 15

Absorbable Polyurethane

The prepolymers in the examples above can be used as prepared, and without chain extension, by terminating the isocyanate groups with a mono-hydroxyl, for example ethanol.

Example 16

Absorbable Polyurethane

Nine grams of Oxymer M112 (carbonate diol, Mn=1500) (Perstorp Specialty Chemicals AB, Perstorp, Sweden) are put into a 3-neck-flask. Toluene is added and partly removed by distillation to get a 20% solution. After cooling to room temperature 0.862 g of hexamethylene diisocyanate are added under nitrogen. 0.6 g of DBTL are added and the mixture is heated to 75° C. After 5 hours the temperature is raised to 80° C. After 10 hours the mixture is allowed to cool to room temperature. The resulting polymer is precipitated in pentane and dried in vacuo. Elongation at break: 800%, Tensile strength: 64 MPa.

Example 17

Six grams of Desmophen 2100 (carbonate diol, Mn=1000) (Bayer, Morristown, N.J.) are put into a 3-neck-flask. Toluene is added and partly removed by distillation to get a 20% solution. After cooling to room temperature 1.513 g of isophorone diisocyanate is added under nitrogen. 0.6 g of DBTL are added and the mixture is heated to 75° C. After 5 hours the temperature is raised to 80° C. After 10 hours the mixture is allowed to cool to room temperature. The resulting polymer is precipitated in pentane and dried in vacuo. Elongation at break: 1040%; Tensile strength: 19 MPa Example 18

Seven grams of Terathane 2000 (Invista, Wichita, Kans.) are put into a 3-neck-flask. Toluene is added and then a part of the toluene is removed by distillation to get a 20% solution. After cooling to room temperature, 2.38 g of isophorone diisocyanate are added under nitrogen. 0.26 g of DBTL are added and the mixture is heated to 75° C. After 5 hours 1.287 g of 1,4-butane diol are added and the reaction mixture is diluted with toluene to get concentration of all components of 15% The temperature is raised to 80° C. After 10 hours the mixture is allowed to cool to room temperature. The resulting polymer is precipitated in pentane and dried in vacuo. Elongation at break: 1870%; Tensile strength: 17 MPa.

Degradation: The material was subjected to an accelerated hydrolytic degradation experiment (2N caustic soda solution at 70° C.). After 4 days the molecular weight was reduced from 73.5 kDa to 61 kDa and the shape of the samples had changed.

Example 19

Forty two grams of Terathane 2000 are put into a 3-neck-flask. Toluene is added and then a part of the toluene is removed by distillation to get a 20% solution. After cooling to room temperature, 14.14 g of isophorone diisocyanate are added under nitrogen. 0.77 g of DBTL are added and the mixture is heated to 75° C. After 4 hours 6.1765 g of 1,4-bis(N-methyl)amino cyclohexane are added and the reaction mixture is diluted with toluene to get concentration of all components of 10% The temperature is raised to 80° C. After 8 hours the mixture is allowed to cool to room temperature. The resulting polymer is precipitated in pentane and dried in vacuo. Elongation at break: 610%; Tensile strength: 62 MPa.

Degradation: The material was subjected to an accelerated hydrolytic degradation experiment (2N caustic soda solution at 70° C.). The mechanical properties were determined each week. Not until 10 weeks a significant reduction of the tensile strength and the elongation at break were observed.

Example 20

Four grams of Terathane 2000 and 4 g of polycaprolactone diol (Mn=2000) are put into a 3-neck-flask. Toluene is added and then a part of the toluene is removed by distillation to get a 20% solution. After cooling to room temperature, 4.05 g of isophorone diisocyanate are added under nitrogen. 0.37 g of DBTL are added and the mixture is heated to 75° C. After 5 hours 1.28 g of 1,4-butane diol are added and the reaction mixture is diluted with toluene to get concentration of all components of 15% The temperature is raised to 80° C. After 10 hours the mixture is allowed to cool to room temperature. The resulting polymer is precipitated in pentane and dried in vacuo. Elongation at break: 990%; Tensile strength: 21 MPa Degradation: The material was subjected to an accelerated hydrolytic degradation experiment (2N caustic soda solution at 70° C.). After 4 days the molecular weight was reduced from 200 kDa to 19 kDa and the shape of the samples had changed. The material was so week that a mechanical characterization was not possible.

Example 21

4.76 g of Terathane 2000 and 6.00 g of polycaprolactone diol (Mn=2000) are put into a 3-neck-flask. Toluene is added and then a part of the toluene is removed by distillation to get a 20% solution. After cooling to room temperature, 3.54 g of isophorone diisocyanate are added under nitrogen. 0.34 g of DBTL are added and the mixture is heated to 75° C. After 5 hours 0.93 g of 1,4-butane diol are added and the reaction mixture is diluted with toluene to get concentration of all components of a 15% The temperature is raised to 80° C. After 10 hours the mixture is allowed to cool to room temperature. The resulting polymer is precipitated in pentane and dried in vacuo. Elongation at break: 1030%; Tensile strength: 28 MPa.

Degradation: The material was subjected to an accelerated hydrolytic degradation experiment (2N caustic soda solution at 70° C.). After 4 days the mechanical properties were only slightly reduced.

In addition, the oxidative degradation was simulated (20% hydrogen peroxide and 2% $CoSO_4$) for 4 days. The mechanical properties were not affected. So 45% nitric acid as a stronger oxidative medium was applied to the material. The polyurethane became yellow and weak after 5 hours.

Example 22

Any of the examples of polymers described thus far can be functionalized by addition of a terminal amine group suitable for attachment of a bioactive substance. One approach is to amine terminate an ether diol and then polymerize this reaction product with an ester. For example, an amine terminated PEG can be synthesized by dissolving the PEG into dry THF at −79° C. utilizing dry ice and methanol as a cooling bath. The amount of amine termination is calculated, and the equivalent amount of 0.25 M solution of potassium-bis-(trimethylsilyl)amide in toluene is then added slowly. The reaction mixture is then stirred at 20° C. for 48 hours. The reaction product is then diluted 10:1 with ether forming a precipitate which can be subsequently separated from solution by filtration. The precipitate is then dissolved in THF and 0.1N hydrochloric acid was added to split the silylamide. The solution is then stirred for 1 hour at room temperature, and then the polymer is precipitated in ether. The resulting NH2-PEG can be polymerized with cyclic DL-dilactide. In the desired ratio, the two ingredients are dissolved separately in dry toluene. The polymerization is accomplished by combining the two solutions under dry nitrogen and heating to boiling. When boil is reached, tin catalyst (tin-2-ethylhexanoate) is then added and reacted for 8 hours. The resulting polymer solution is cooled and mixed with dichloromethane to remove water by evaporation. The dicholoromethane of the dry solution is exchanged with acetone and the resulting solution dripped into distilled water at 0° C. and the resulting precipitate collected.

These and other considerations described in the present disclosure are meant to be illustrative of practicing the present disclosure, and are not meant to limit its scope.

What is claimed is:

1. A bioabsorbable polyurethane comprising a polymerization product of a prepolymer and a chain extender:
   the polymerization product comprising polylactic acid diol, having a Mn of 1000, polyethylene glycol, having a Mn of 2000, isophorone diisocyanate, and
   the chain extender is 1,4-butane diol, wherein a mole ratio with respect to the polylactic acid diol, polyethylene glycol, isophorone diisocyanate, and 1,4-butane diol is 2:1:10.1:7.1 respectively, and
   wherein the bioabsorbable polyurethane degrades at a rate which retains 88% total molecular weight of the composition after 1 week as determined by storage in phosphate buffer solution at 37° C.

2. The bioabsorbable polyurethane of claim 1, wherein the polylactic acid comprises poly(L-lactic acid), poly(D,L-lactic acid), or a combination thereof.

3. The bioabsorbable polyurethane of claim 1, wherein the bioabsorbable polyurethane provides an anti-adhesion barrier when disposed about tissue.

4. The bioabsorbable polyurethane of claim 3, wherein the polylactic acid diol and polyethylene glycol are arranged so that hydrophobic interactions with proteins is blocked.

5. The bioabsorbable polyurethane of claim 3, wherein the bioabsorbable polyurethane is formed into an implantable sheet wherein the implantable sheet comprises a first side and a second side, wherein the first side includes the anti-adhesion barrier and the second side includes a cellular ingrowth support surface.

6. A bioabsorbable polyurethane comprising a polymerization product of a prepolymer and a chain extender:
the polymerization product comprising polylactic acid diol, having a Mn of 1000, polytetramethylene ether glycol, having a Mn of 2000, isophorone diisocyanate, and
the chain extender is 1,4-butane diol, wherein a mole ratio with respect to the polylactic acid diol, polytetramethylene glycol, isophorone diisocyanate, and 1,4-butane diol is 4:1:20.2:14.2 respectively, and
wherein the bioabsorbable polyurethane degrades at a rate which retains 50% total molecular weight of the composition after 1 week as determined by storage in phosphate buffer solution at 37° C.

7. The bioabsorbable polyurethane of claim 6, wherein the polylactic acid comprises poly(L-lactic acid), poly(D,L-lactic acid), or a combination thereof.

8. The bioabsorbable polyurethane of claim 6, wherein the bioabsorbable polyurethane provides an anti-adhesion barrier when disposed about tissue.

9. The bioabsorbable polyurethane of claim 8, wherein the polylactic acid diol and polytetramethylene ether glycol are arranged so that hydrophobic interactions with proteins is blocked.

10. The bioabsorbable polyurethane of claim 8, wherein the bioabsorbable polyurethane is formed into an implantable sheet wherein the implantable sheet comprises a first side and a second side, wherein the first side includes the anti-adhesion barrier and the second side includes a cellular ingrowth support surface.

* * * * *